United States Patent
Chen et al.

(10) Patent No.: US 10,147,207 B2
(45) Date of Patent: Dec. 4, 2018

(54) SYSTEM AND METHOD FOR HIGH-TEMPORAL RESOLUTION, TIME-RESOLVED CONE BEAM CT ANGIOGRAPHY

(71) Applicant: Wisconsin Alumni Research Foundation, Madison, WI (US)

(72) Inventors: Guang-Hong Chen, Madison, WI (US); Charles Strother, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 322 days.

(21) Appl. No.: 15/211,448

(22) Filed: Jul. 15, 2016

(65) Prior Publication Data

US 2018/0018796 A1    Jan. 18, 2018

(51) Int. Cl.
*G06T 11/00* (2006.01)
*A61B 6/00* (2006.01)
*A61B 6/03* (2006.01)

(52) U.S. Cl.
CPC ............ *G06T 11/006* (2013.01); *A61B 6/032* (2013.01); *A61B 6/4085* (2013.01); *A61B 6/4441* (2013.01); *A61B 6/504* (2013.01); *A61B 6/5217* (2013.01); *G06T 11/008* (2013.01); *A61B 6/481* (2013.01); *G06T 2211/404* (2013.01); *G06T 2211/421* (2013.01)

(58) Field of Classification Search
None
See application file for complete search history.

(56) References Cited

U.S. PATENT DOCUMENTS

| | | |
|---|---|---|
| 8,194,937 B2 | 6/2012 | Chen |
| 8,229,199 B2 | 7/2012 | Chen et al. |
| 8,374,413 B2 | 2/2013 | Chen |
| 2014/0228674 A1* | 8/2014 | Chen ...................... A61B 6/486 600/420 |
| 2014/0270439 A1 | 9/2014 | Chen |

\* cited by examiner

*Primary Examiner* — Matthew Bella
*Assistant Examiner* — Brian Shin
(74) *Attorney, Agent, or Firm* — Quarles & Brady LLP (57) ABSTRACT

A system and method for reconstructing an image using a cone-beam computed tomography (CT) imaging system includes acquiring data from a subject with the CT imaging system using a limited scan range that is less than 360 degrees. The process also includes reconstructing at least one image of the subject having a first temporal resolution from the data acquired, performing a temporal deconvolution of the at least one image using a finite temporal window to generate at least one image of the subject with a second temporal resolution that is greater than the first temporal resolution, and subtracting the at least one image of the subject with the second temporal resolution and a mask image of the subject to generate a time-resolved CT angiogram of the subject.

20 Claims, 6 Drawing Sheets

FIG. 8

SYSTEM AND METHOD FOR HIGH-TEMPORAL RESOLUTION, TIME-RESOLVED CONE BEAM CT ANGIOGRAPHY

STATEMENT REGARDING FEDERALLY SPONSORED RESEARCH

This invention was made with government support under EB021183 awarded by the National Institutes of Health. The government has certain rights in the invention.

BACKGROUND

The present disclosure relates to systems and methods for medical image reconstruction. More particularly, systems and method are provided for generating high-temporal resolution, time-resolved cone beam computed tomography (CT) angiographic images.

Image-based guidance of therapeutic devices, such as catheters, and/or the placement of interventional devices, such as guidewires and stents is a key component of modern medicine. Currently, x-ray digital subtraction angiography (DSA) and x-ray fluoroscopy are the gold standard for such image-guided procedures. For example, the tips of guidewires can be easily visualized using conventional x-ray fluoroscopy by applying small, radio-opaque markers to the tips. As another example, DSA helps visualize and locate the vascular abnormalities and plays a critically important role in diagnosis and treatment planning processes.

Of course, both DSA and x-ray fluoroscopy have substantial limitations, such as its inability to resolve in three dimensions or select specific two-dimensional slices. As such, it is common for the clinical workflow to include imaging acquisitions with computed tomography (CT) systems or other multi-dimensional anatomical imaging systems before interventional medical procedures or, in some cases, even during an interventional medical procedure. Unfortunately, such multi-dimensional or high-temporal or spatial resolution anatomical imaging systems are generally located in dedicated imaging rooms or facilitates, due to the size and operational complexity of such systems. As a result, in some cases, it can be necessary to move patients, even repeatedly, from examination rooms, to imaging rooms, to operating rooms, and therebetween to perform successful patient care. Even in specialized settings where the desired imaging systems may be integrated into an operating room or other facility, the patient care, which may include an interventional procedure, must often be interrupted to perform the imaging process, for example, to locate the region of the patent under consideration within the imaging gantry of a CT system. Unfortunately, this disjointed workflow can be required with patients that are ill-equipped to endure the repeated moves between rooms or the delays caused by the moves, for example, in trauma patients or patients with cardiac or cardiovascular failures.

As such, it would be desirable to have systems and methods that could provide clinical caregivers with the desired imaging data, without requiring repeated moves, delays, or general interference with patient care. Thus, some of the newer generation x-ray angiographic systems offers the CT-like data acquisition and reconstruction in the x-ray angiographic suite where the medical treatment procedure takes place.

X-ray projection images encode the variations of the x-ray attenuation properties of an image object into the transmitted x-ray photons to produce the shadow image of the object. However, tissues may be superimposed in the projection image, degrading the diagnostic performance. When the specific anatomy such as vascular structures become the focus of the clinical task, a variety of subtraction techniques can be introduced to remove the overlapping structures that are not relevant to the clinical task from the projection image. In the applications of contrast enhanced angiography, two images, one with contrast enhancement (filled) and one without (mask), can be subtracted to generate angiograms to bring the targeted vasculature into the focus of clinical diagnosis. Although the idea of the temporal subtraction of two images is not new in modern digital imaging, it was DSA that first provided the clinically needed image quality to revolutionize the modern image-guided interventional procedures. Currently, DSA is an indispensable imaging tool in angiographic suites and the current clinical gold standard for the diagnosis and image-guided interventions of vascular abnormalities, including occlusions, stenoses, aneurysms, and so forth.

Although anatomical superposition has been greatly alleviated in two dimensional DSA (2D-DSA), the intrinsically three-dimensional (3D) complex vascular structures may still superpose in 2D-DSA images. Thus the acquisition of multiple DSA images from several gantry angles is often needed to provide physicians adequate 3D visualization and understanding of complex vasculature. The desire to remove the structural overlaps in 2D-DSA motivated the idea and experimental implementation of 3D-DSA via tomographic reconstruction, which were initially acquired using image intensifiers and are currently acquired using digital flat-panel detectors. Note that 3D-DSA has also been referred to as 3D rotational angiography in literature. In clinical practice, the introduction of 3D-DSA in interventional suite has been found to have great value in diagnosis and in providing image-guidance to the treatment of vascular diseases with improved sensitivity and specificity.

However, a general feature of these so-called C-arm cone beam CT data acquisition systems is slow in data acquisition due to the safety concerns of open gantry C-arm data acquisition platforms. As a result, such systems intrinsically lack dynamic information provided by the current 3D-DSA images acquired from these C-arm cone beam CT data acquisition systems.

SUMMARY

The present disclosure overcomes the aforementioned drawbacks by providing systems and methods for reconstructing high temporal resolution time-resolved cone-beam CT angiographic images using a cone-beam CT imaging system. As will be described, a "SMART RECON" process is used to reconstructed data acquired from a subject with the cone beam CT imaging system using a limited scan range that is less than 360 degrees to create multiple images at a first temporal resolution. A temporal deconvolution is performed using the generated multiple images with a finite temporal window to generate multiple images of the subject with a second temporal resolution that is greater than the first temporal resolution. A subtraction is performed between the multiple reconstructed images of the subject with the second temporal resolution and a mask image of the subject to generate a time-resolved CT angiogram of the subject at the second temporal resolution.

In accordance with one aspect of the disclosure, a method is provided for reconstructing an image using a cone beam computed tomography (CT) imaging system. The steps of the method include a) acquiring data from a subject with the CT imaging system using a limited scan range that is less than 360 degrees, b) initializing an image matrix having columns that each correspond to a different image and c) reconstructing at least one image of the subject having a first temporal resolution from the data acquired in step a). The reconstructing is performed by i) minimizing a matrix rank of the image matrix, ii) constraining the rank minimization of step c)i) subject to a consistency condition that promotes a forward projection of each column in the image matrix to be consistent with a different subset of the acquired data, each subset of the acquired data containing data that are consistent with each other while being inconsistent with data in other subsets of the acquired data. The method further includes d) performing a temporal deconvolution of the at least one image using a finite temporal window to generate at least one image of the subject with a second temporal resolution that is greater than the first temporal resolution and e) subtracting the at least one image of the subject with the second temporal resolution and a mask image of the subject to generate a time-resolved CT angiogram of the subject.

In accordance with another aspect of the disclosure, a method is provided for reconstructing an image using a cone beam computed tomography (CT) imaging system. The steps of the method include a) acquiring data from a subject with the CT imaging system, the acquired data acquired using a short scan of less than 360 degrees and containing a plurality of data consistency classes and b) reconstructing an image of the subject from the data acquired in step a), the image of the subject containing artifacts associated with the data inconsistencies. The method further includes c) forming an image matrix having a first column corresponding to the image reconstructed in step b), d) computing a target image matrix by iteratively updating the image matrix formed in step c) by minimizing a matrix rank of the image matrix subject to a data consistency condition such that each column of the computed target image matrix corresponds to a different one of the plurality of data consistency classes and e) providing each column of the target image matrix computed in step d) as an image of the subject that is substantially free of artifacts to produce a series of images of the subject at a first temporal resolution. The method further includes f) deconvolving the series of images of the subject at the first temporal resolution using a finite temporal window to generate a series of images of the subject with second temporal resolution that is higher than the first temporal resolution and g) subtracting the series of images of the subject with the second temporal resolution and from mask images of the subject to generate a time-resolved CT angiogram of the subject.

In accordance with yet another aspect of the disclosure, a cone beam computed tomography (CT) system is provided that includes an x-ray source and associated detectors configured to acquire imaging data from a subject over a range of view angles. The CT system also includes a computer system including a processor configured to a) control operation of the x-ray source and associated detectors to acquire data from a subject with the CT imaging system using a limited scan range that is less than 360 degrees, b) initialize an image matrix having columns that each correspond to a different image, and c) reconstruct at least one image of the subject having a first temporal resolution from the data acquired in step a). This reconstruction is performed by i) minimizing a matrix rank of the image matrix and ii) constraining the rank minimization of step c)i) subject to a consistency condition that promotes a forward projection of each column in the image matrix to be consistent with a different subset of the acquired data, each subset of the acquired data containing data that are consistent with each other while being inconsistent with data in other subsets of the acquired data. The processor is further configured to d) perform a temporal deconvolution of the at least one image using a finite temporal window to generate at least one image of the subject with a second temporal resolution that is greater than the first temporal resolution and e) subtract the at least one image of the subject with the second temporal resolution and a mask image of the subject to generate a time-resolved CT angiogram of the subject.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

Fig. is a schematic diagram of a C-arm x-ray computed tomography (CT) imaging system configured in accordance with the present disclosure.

DETAILED DESCRIPTION

Figure 1:
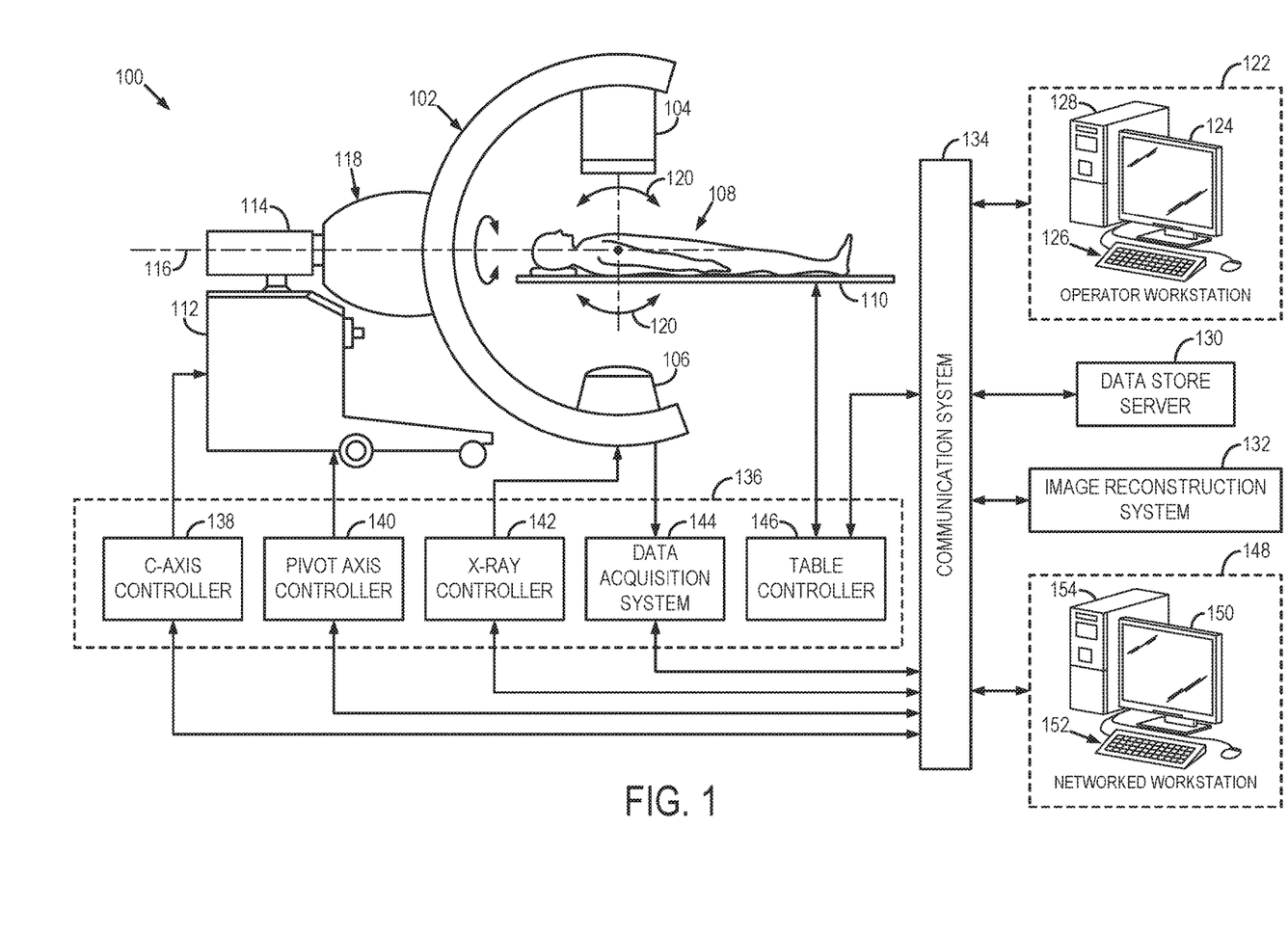
Figure 2:
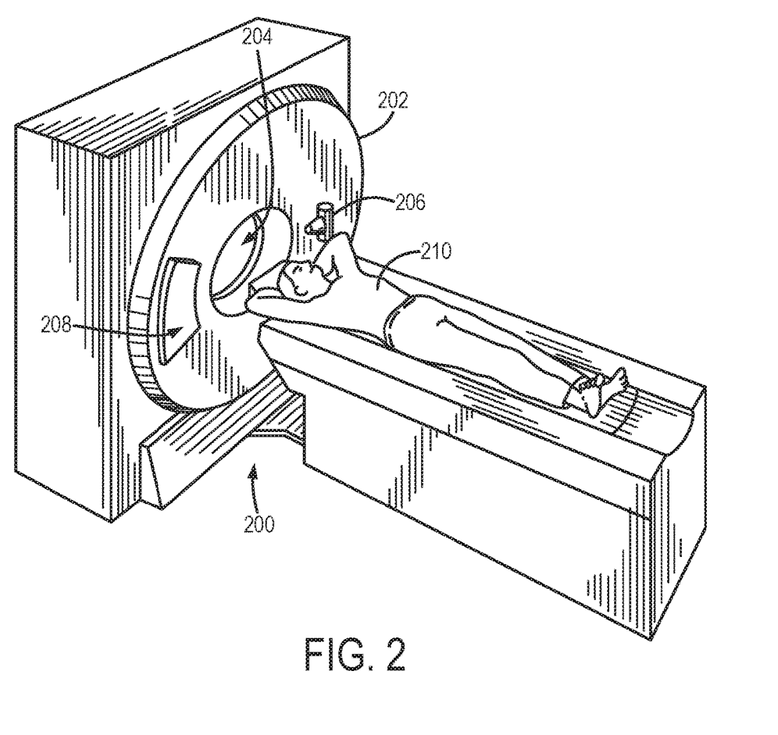
FIG. 2 is a perspective view of an example of an x-ray computed tomography (CT) system.

Referring to FIG. 1, an example of a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2. That is, the traditional CT system includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202. Thus, when a subject 210 is arranged in the bore 204 for imaging using the source 206 and detector array 208, access to the subject 210 is restricted by the gantry 202.

Referring again to FIG. 1, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

With conventional image reconstruction techniques, such as filtered backprojection for CT/C-arm CT imaging and Fourier-based reconstructions techniques for magnetic resonance imaging (MRI), a single image is reconstructed from a corresponding set of data acquired with the medical imaging system. For example, one image is reconstructed from a single sinogram in x-ray CT/C-arm CT imaging and one image is reconstructed from one k-space data set in MRI. This correspondence between data and the images reconstructed from that data is a function of traditional image reconstruction techniques and the fact that such techniques are based on an assumption that all of the acquired data are consistent with each other. Routinely, however, data acquired with medical imaging systems are not consistent with a single true image of the subject being imaged, or a single state of a true image object that has dynamic characteristics.

These inconsistencies manifest as artifacts in the reconstructed images and can have many different origins. For example, in x-ray CT/C-arm CT imaging, artifacts can result from the presence of metal objects in the subject, by acquiring too few projections, from beam-hardening effects, from x-ray scattering, subject motion, and so on. In MRI, artifacts can result from undersampling k-space, magnetic field inhomogeneities, subject motion, and so on. Inconsistencies between the acquired data and the stationary state of a true image of the subject can also have other sources, such as the presence of an exogenous contrast agent that if administered to the subject and the travels through the subject's vasculature. The assumption that the reconstructed image should be consistent with the acquired data is embodied in the following imaging model:

$$AI=Y \qquad (1);$$

which states that image reconstruction techniques should seek to reconstruct an image, I, that when forward projected is consistent with the acquired data, Y. The matrix, A, is referred to as the system matrix, which can be generally regarded as a forward projection operator that relates the reconstructed image, I, to the acquired data samples, Y. Eqn. (1) imposed that the reconstructed image, I, must be consistent with the measured data samples, Y; thus, Eqn. (1) can also be referred to as the "data consistency condition." In x-ray CT imaging, the system matrix can include a reprojection operation and in MRI the system matrix can include a Fourier transform operation. The consistency condition of Eqn. (1), put in other words, states that when an image is faithfully reconstructed, the forward projection of that image should be substantially similar to, or consistent with, the data actually acquired with the imaging system.

To reconstruct an image, I, from the measured data, Y, it is often required that the data satisfy the so-called data sufficiency condition, which is a condition that allows for an inverse reconstruction formula to be used to reconstruct the image from the measured data. In x-ray CT imaging, the data sufficiency condition is the so-called Tuy condition, which requires the data samples to be acquired in an extended angular range around the image object. In MRI, the data sufficiency condition is the complete population of the entire Fourier space. Even when the data sufficiency condition is satisfied, however, still another condition needs to be met to reconstruct a true image of the image object. The discretely acquired data samples also need to satisfy the associated sampling criterion for a given reconstruction scheme.

Examples of data sampling criteria include the view angle sampling requirement in x-ray CT and the Nyquist sampling criterion in MRI. When the data sampling criterion is met in x-ray CT, filtered backprojection can be used to reconstruct an image, and when the data sampling criterion is met in MRI, Fourier inversion can be used to reconstruct an image. When an iterative image reconstruction method is employed, the data sampling criteria are often significantly relaxed. One example of such a method is compressed sensing based iterative image reconstruction techniques.

In an ideal situation, when the aforementioned data sufficiency condition and data sampling conditions are satisfied, an artifact-free image can be reconstructed. This ideal situation is impractical in the real world, however, due to complications of data acquisition conditions and complications from the objects being imaged. As a result of these complications, the acquired data may not represent the same physical state of the image object, or may not be acquired under the same physical conditions. Thus, the acquired data are referred to as "inconsistent data." The physical reasons for these inconsistencies, whether because of a non-ideal acquisition system or because of a change in the physical state of the object during data acquisition, are referred to as the sources of inconsistency.

When the acquired data are no longer consistent due to sources of inconsistency, such as those described above, the consistency condition begins to break down. That is, the acquired data are no longer consistent when physical effects such as subject motion, contrast enhancement, noise, beam hardening in x-ray imaging, and so on are present during the data acquisition process. The inconsistencies in the acquired data manifest as artifacts in the reconstructed images.

Described here are systems and methods for generating time-resolved CT angiography with selectably high temporal resolution. The system and method can leverage a process for simultaneous image artifact reduction and tomographic image reconstruction, which may thus be referred to as a "SMART-RECON." As will be described, SMART RECON can be applied to reconstruct multiple cone-beam CT images from a single-pass cone beam CT data set. The systems and methods are advantageously suited for medical imaging applications, such as time-resolved computed tomography ("CT"), cone-beam CT, cardiac imaging CT, contrast-enhanced CT, and x-ray angiography, and, particularly, provides the ability to simplify the way time-resolved images for interventional procedures are acquired and ease clinical workflow. The present systems and methods can be used to reduce radiation dose and contrast dose and, as a result, enhance patient safety, since only IV contrast injection is needed. The process can be performed at outpatient clinics.

In general, the image reconstruction operates by minimizing the rank of a generalized matrix that contains the target image and other images that are associated with acquired data that have different degrees of consistency. This method, and several examples of its implementation, are described below in detail.

With conventional image reconstruction techniques, such as filtered backprojection for x-ray CT imaging and Fourier-based reconstruction techniques for MRI, one image is reconstructed from one data set, despite the existence of data inconsistencies. For example, one image is reconstructed from a single sinogram in x-ray CT imaging and one image is reconstructed from one k-space data set in MRI. This correspondence between data and the images reconstructed from that data is because these traditional image reconstruction techniques are based on the assumption that all of the acquired data are consistent with each other and satisfy the sufficiency condition. By way of example, data acquired with an x-ray CT imaging system lose their consistency when the subject moves during data acquisition, when an exogenous contrast agent is administered to the subject, and when the x-ray beam is no longer monochromatic (e.g., when beam-hardening occurs). Again, this assumption is embodied in the so-called forward imaging model, or "consistency condition" of Eqn. (1).

Conventional image reconstruction methods, such as filtered backprojection for x-ray CT, Fourier inversion for MRI, and iterative reconstruction from all acquired data, there is no intrinsic mechanism that accounts for the degree of data consistency or inconsistency. The single indication of data inconsistency is the appearance of image artifacts in the reconstructed image. To reduce the artifact levels, the acquired data can be preprocessed with the appropriate technique for the type of artifacts present in the image. It is unknown, however, to what extent the acquired data should be corrected before image reconstruction.

It is noted that tomographic reconstructions, such as filtered backprojection, have a certain level of tolerance to data inconsistencies. For example, data inconsistency may not necessarily result in image artifacts in the reconstructed image, but the threshold for this tolerance to inconsistencies cannot be known a priori. Thus, it remains highly desirable to develop systems and methods that can automatically account for data inconsistencies during the image reconstruction process.

The acquired data are no longer consistent when physical effects such as subject motion, contrast enhancement, noise, beam hardening in x-ray imaging, and so on are present during the data acquisition process. These inconsistencies in the acquired data manifest as artifacts in the reconstructed images.

To address this problem, the present disclosure provides systems and methods for image reconstruction that account for intrinsic data consistency in acquired data, which allows for images to be separately reconstructed with different artifact levels that depend on the inconsistency level of the acquired data. In many cases, an image with minimal artifacts will be reconstructed from those consistent data samples, together with an image that primarily depicts artifacts from other data with higher levels of inconsistency in the acquired data.

This concept can be interpreted as seeking to reconstruct the maximally available generalized image matrix, X, from the acquired data. If the acquired set of data samples has $N_S$ data samples, the worst case scenario is that all of the data samples are inconsistent with one another. In this case, $N_S$ images would be required to delineate the physical state of the image object. As a result, the maximally available generalized image matrix, X, would have $N_S$ columns. The number of rows in the maximally available generalized image matrix, X, would be the total number of image pixels for a two-dimensional image, or the total number of image voxels for a three-dimensional image volume. By lowering the rank of this generalized image matrix while constrained by the data consistency condition of Eqn. (1), the images with different artifact levels can be reconstructed by automatically grouping consistent data into a series of images that reflects the consistency level among the data.

The connection between data consistency and image matrix rank reduction can be understood as follows. When the acquired data are all consistent (e.g., from each view angle in x-ray CT imaging or with respect to each line in k-space in MRI), all columns in the maximally available generalized image matrix, X, will be the same. Mathematically, this generalized image matrix, X, thus has a column rank of one, or Rank(X)=1. When the acquired data can be divided into two consistency classes in some way, then the rank of the maximally available generalized image matrix, X, will increase to two, or Rank(X)=2. In this instance, the rank of the maximally available generalized image matrix can be reduced to two. In other words, the rank reduced generalized image matrix, X, contains only two columns, $$X=[X_1 \, X_2] \quad (2);$$

where each column corresponds to an image reconstructed from the data in the associated consistency class.

The increase in rank is because the acquired data contains two distinct groups of data that are each internally consistent, but inconsistent with each other. An example of this is when data is acquired from a subject who moves during data acquisition. The data acquired when the subject was not moving will not be consistent with the data acquired when the subject was moving. On the other hand, the data acquired when the subject was not moving will be internally consistent, as will the data acquired when the subject was moving. This property is exploited by the present disclosure to reconstruct an image that is free of the contributions from the inconsistent data. As will be described below, there can be more than two consistency classes in the acquired data and each of these consistency classes can be separated from each other.

In general, an image that is free of the contributions from inconsistent data can be obtained by minimizing the rank of the maximally available generalized image matrix, X, such that the forward projection of the desired column of the maximally available generalized image matrix, $X_n=I_n$, is consistent with the associated consistency class in the acquired data, $Y_n$. That is, $$\underset{X}{\operatorname{argmin}}\{\operatorname{Rank}(X)\} \text{ such that } AI_n = Y. \quad (3)$$

The rank minimization described by Eqn. (3) automatically and iteratively groups consistent data from different sources into several irreducible image columns in X. It is noted that the individual image, $I_n$, corresponds to a different consistency class and is a column vector in the generalized image matrix, X. That is, $$X=[I_1 \ldots I_N] \quad (4).$$

Here, the individual image, $I_n$, corresponding to a particular consistency class is formed by applying a vectorization operation to an ordinary image with two indices, $$I_n=vec(I_n(x,y)) \quad (5);$$

or with three indices, $$I_n=vec(I_n(x,y,z)) \quad (6).$$

Numerically, it is an NP-hard problem to solve the rank minimization problem because it is equivalent to solving a zero-norm minimization problem. This point can be illustrated by introducing a singular value decomposition ("SVD") operation to the generalized image matrix, X, as follows:

$$X = U\Sigma V \quad (7);$$

where the U and V matrices are orthogonal and the $\Sigma$ matrix is a diagonal matrix with r non-zero elements, referred to as the singular values, $\sigma_i$, of the matrix, $$\Sigma = \mathrm{diag}\{\sigma_1, \sigma_2, \ldots, \sigma_r, 0, 0, \ldots, 0\} \quad (8).$$

As long as this SVD is performed, the rank of the generalized image matrix, X, is said to be r. Thus, minimization of the rank of the generalized image matrix, X, can be equated to minimizing the following zero-norm:

$$\operatorname*{argmin}_{X}\{\mathrm{Rank}(X)\} \equiv \operatorname*{argmin}_{X} \|X\|_0; \quad (9)$$

where $\|X\|_0$ is the zero-norm of the generalized image matrix, X, which is equal to the number of non-zero diagonal elements in the singular value decomposition of the generalized image matrix, X. The zero-norm problem in Eqn. (9) can be practically relaxed to an $l_1$-norm, as is often done in compressed sensing. Namely, instead of directly solving the problem in Eqn. (3), the problem is relaxed to the following convex optimization problem:

$$\operatorname*{argmin}_{X} \|X\|_*; \quad (10)$$

where $\|X\|_*$ is the so-called nuclear norm of the generalized image matrix, X, which can be given by, $$\|X\|_* = \sum_{i=1}^{r} |\sigma_i| = \sum_{i=1}^{r} \left| \sum_{ii} \right|. \quad (11)$$

More generally, the more general Schatten p-norm can be used to relax the precise rank minimization in Eqn. (3). The Schatten p-norm is defined as, $$\|X\|_p^p = \sum_{i} \sigma_i^p. \quad (12)$$

Using the Schatten p-norm, the rank minimization in Eqn. (3) can be relaxed as the following convex optimization problem for $p \geq 1$:

$$\operatorname*{argmin}_{X} \|X\|_p^p \text{ such that } AI_n = Y. \quad (13)$$

The constrained optimization problem in Eqn. (13) can be solved by minimizing the following objective function with a quadratic penalty:

$$\operatorname*{argmin}_{X} \left\{ \frac{1}{2} \|AI_n - Y\|_D^2 + \lambda \|X\|_p^p \right\}; \quad (14)$$

where the weighted norm for a generalized input is given as, $$\|Z\|_D^2 = Z^T D \quad (15);$$

with the diagonal matrix, D, given by, $$D = \mathrm{diag}\left\{ \frac{1}{\xi_1^2}, \frac{1}{\xi_2^2}, \ldots \right\}; \quad (16)$$

where $\xi_i^2$ is the noise variance for the $i^{th}$ measured data sample. Therefore, the diagonal matrix, D, accounts for noise in the measured data samples by assigning a lower weight to higher noise data and a higher weight to lower noise data. The parameter, $\lambda$, is used to tradeoff the data fidelity term and the relaxed matrix rank minimization term in Eqn. (14). The equivalence of the constrained optimization problem in Eqn. (13) and the unconstrained optimization problem in Eqn. (14) can be reached in the limit of $\lambda = \infty$. Additionally, the constrained optimization problem in Eqn. (13) can be solved using the well-known augmented Lagrangian multiplier method.

In Eqn. (14), rank minimization can be viewed as a regularization to the noise-penalized least square minimization. In addition to the above rank regularization, other additional regularization methods can also be added to Eqn. (14). One example of additional regularization methods includes the prior image constrained compressed sensing ("PICCS") objective function, which is described in U.S. Pat. Nos. 8,194,937; 8,229,199; and 8,374,413, which are each herein incorporated by reference in their entirety. By incorporating the PICCS objective function, Eqn. (14) can be generalized as, $$\operatorname*{argmin}_{X} \left\{ \frac{\lambda}{2} \|AI_n - Y\|_D^2 + \|X\|_p^p + \alpha \|\Psi_1 I_n\|_q^q + (1-\alpha) \|\Psi_2 (I_n - I_P)\|_q^q \right\}; \quad (17)$$

where $\Psi_1$ and $\Psi_2$ are sparsifying transforms, which promote sparsity in each individual image component, $I_n$; $I_P$ is a prior image in the PICCS reconstruction; the parameter, $\alpha$, is used to assign a weight to the term without the prior image contribution and to the term with the prior image contribution; and the q-norm of a vector, Z, is defined as, $$\|Z\|_q^q = \sum_{j=1}^{N} |Z_j|^q. \quad (18)$$

When a blind SVD operation is applied to the generalized image matrix, X, it can be computationally expensive. In practice, it is contemplated that the target rank of the generalized image matrix will generally be low; thus, a truncated SVD decomposition can be used in a numerical implementation. As one example, the lowest rank approximation can be used, in which Rank(X)=1. In this case, all of the acquired data samples are used to reconstruct a single image. The conventional numerically efficient methods for solving such a problem is an image reconstruction technique such as filtered backprojection for x-ray CT data or Fourier inversion for k-space data acquired with an MRI system. This first pass estimation can be used as the initial guess for the first column of the generalized image matrix, X. The rank minimization process can then iteratively proceed to rank two, rank three, an upwards to the desired rank r solution. In practice, it is contemplated that r≤20 will be sufficient for most clinical imaging applications. In this case, the acquired data are sorted into r different consistency classes. Using the first column as the prior image, $I_P$, the PICCS algorithm can be used to reconstruct the r columns of the generalized image matrix, X. Having obtained these initial solutions, the generalized image matrix, X, can be decomposed into the following form:

$$X = [I_1 \ I_2 \ \ldots \ I_{N-1} \ I_N]$$ (19)

$$= U^{MN \times r} \sum\nolimits^{r \times r} V^{r \times MN}.$$

Here, the initially estimated r column images fill in the r columns in the U matrix. One of the optimization problems in Eqns. (3), (10), (13), (14), or (17) can be solved to iteratively determine the diagonal matrix, Σ, and also the V matrix. Furthermore, if the multiplication of the diagonal matrix, Σ, and the V matrix is treated as a single matrix, $$\tilde{V}^{r \times MN} = \Sigma V$$ (20);

then the optimization problem in Eqns. (3), (10), (13), (14), or (17) can then be solved iteratively to determine the matrix, $\tilde{V}$.

When the above decomposition of the generalized image matrix, X, is performed such that the image matrix, X, is decomposed into the following matrix multiplication:

$$X = UV$$ (21);

sparsity constraints and other regularizations can be directly applied to the two matrix components, U and V. As a result, the following variation in the optimization problem can be provided.

$$\underset{X}{\mathrm{argmin}} \left\{ \frac{1}{2} \|AI_n - Y\|_D^2 + \lambda_1 \|\Psi_1 U\|_1 + \lambda_2 \|\Psi_2 V\|_1 \right\}.$$ (22)

When the above described procedure to compute the U matrix is used, the second term in Eqn. (22), $\lambda_1 \|\Psi_1 U\|$, can be set to zero to improve numerical efficiency.

For instance, in an x-ray CT imaging application, the rank minimization will automatically and iteratively group consistent data from different view angles into several irreducible image columns. The numerical value of the final rank of the generalized image matrix, X, is the number of distinct images that are reconstructed from the acquired data. Each of these distinct images corresponds to a different subset of the acquired data that is internally consistent.

Classification of data consistency classes will depend on the particular imaging application. In an x-ray CT application, data samples acquired at each given x-ray source position often represents a consistency class when dynamic CT imaging is performed. Examples of dynamic CT imaging includes cardiac CT imaging in diagnostic multislice CT; contrast-enhanced CT imaging, with or without organ motion involved; time-resolved cone-beam CT in image-guided radiation therapy; an time-resolved cone-beam CT using a C-arm based cone-beam CT system in image-guided interventions.

When multi-energy CT acquisitions are employed, the consistency classification will be dependent on the x-ray spectrum. Thus, for dual energy CT acquisitions, it is natural to classify the data and images into two consistency classed corresponding to the two energy levels utilized in the imaging procedure.

When a conventional single spectrum CT data acquisition is used, the data and images can be classified into two or more classes that are determined by the x-ray path lengths and image content. When highly attenuating objects, such as bony structures or exogenous metallic objects, are present in the subject, the measured data points passing though these highly attenuating objects and those measured data that do not pass through these highly attenuating objects can be classified into different consistency classes.

For an MRI system that is used to generate dynamic imaging, such as cardiac MRI or time-resolved contrast-enhanced MRI, the data consistency and corresponding image classes can be sorted based on prior knowledge of the cardiac and/or respiratory phase.

The higher the rank of the maximally available generalized image matrix, X, the more consistency classes that will be sought in the acquired data. That is to say, as the rank of the maximally available generalized image matrix, X, increases, the inconsistencies in the acquired data will be spread to more images. Depending on the imaging application, this feature can be advantageously relied upon to separate a general class of inconsistency into smaller subsets. For example, motion artifacts can be parsed into motions occurring at different speeds. In this manner, slower motion artifacts (e.g., respiratory motion) can be separated from faster motion artifacts (e.g., cardiac motion).

The rank minimization can also be combined with other minimization constraints to further improve image quality. For instance, the minimization presented in Eqn. (3) can be additionally constrained subject to conditions or optimization requirements. One example of an additional constraint is a prior image constrained compressed sensing ("PICCS") constraint, such as the ones described in U.S. Pat. Nos. 8,194,937; 8,229,199; and 8,374,413, which are each herein incorporated by reference in their entirety. Alternatively, other compressed sensing constraints could be imposed while minimizing the rank of the maximally available image matrix.

Advantageously, minimizing the rank of the maximally available image matrix in this manner allows for the separation of unwanted components of an image from the desirable components. In some instances, the unwanted components can then be used to further correct the desirable components or to ascertain additional information about the subject. Several applications of this method will now be described.

Figure 3:
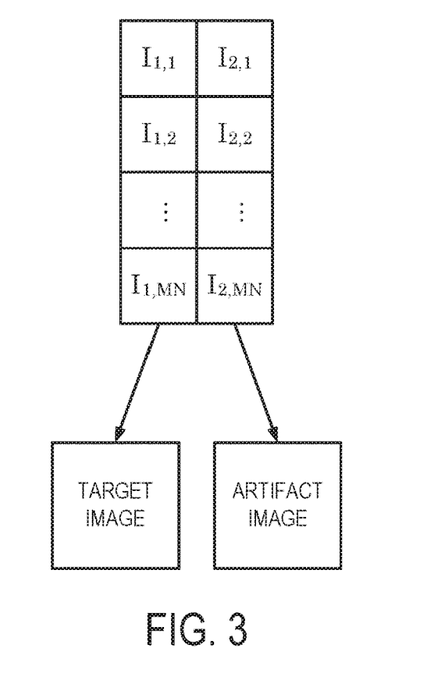
FIG. 3 is an illustration of an example of a rank-minimized image matrix having columns associated with a target image of a subject and an artifact image.

With reference now to FIG. 3, the above-described SMART RECON method can be used to produce a rank R=2 maximally available image matrix, X, having two columns corresponding to two consistency classes of the acquired data. The first column contains the target image, in which substantially no image artifacts are present. The second column contains an artifact image that depicts the inconsistencies in the acquired data, which are generally regarded as image artifacts. For instance, this artifact image can include contributions associated with streak artifacts, aliasing artifacts, scatter artifacts, beam hardening artifacts, motion artifacts, and so on. As one example, when metal artifacts and beam hardening corrupt CT images, the method of the present disclosure is capable of searching for a target image with minimal metal and beam hardening artifacts while also optionally returning other images that depict primarily only the respective artifacts.

Figure 4:
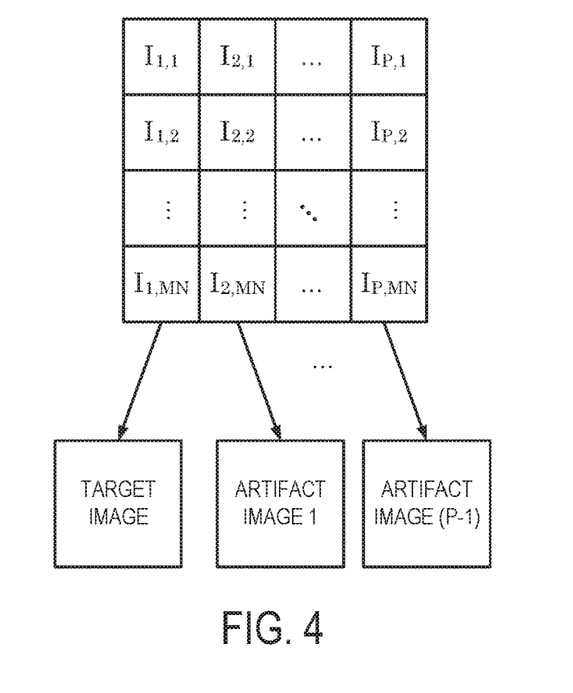
FIG. 4 is an illustration of an example of a rank-minimized image matrix having columns associated with a target image of a subject and multiple different artifact images.
Figure 5:
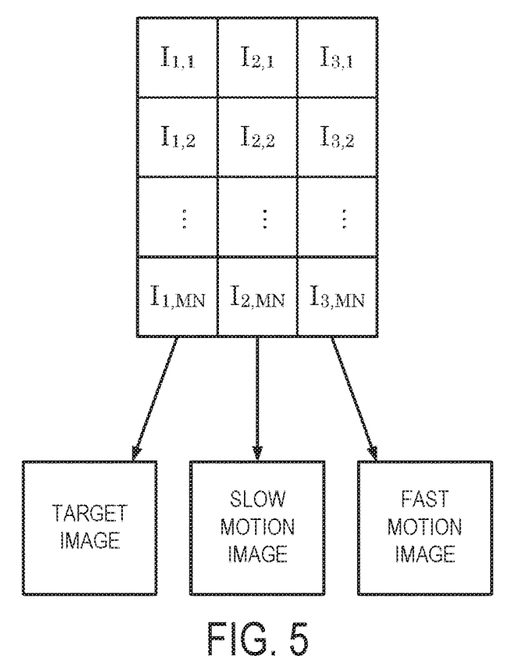
FIG. 5 is an illustration of an example of a rank-minimized image matrix having columns associated with a target image of a subject, an image associated with fast motion occurring within the subject during data acquisition, and an image associated with slower motion occurring within the subject during data acquisition.

As illustrated in FIG. 4, the above-described SMART RECON method can also be used to further separate an artifact image into multiple different artifact images by selecting the appropriate rank at which to conclude the rank minimization of the maximally available image matrix. For instance, the method of the present disclosure can be used to separate different artifacts into different images, such as one image for streak artifacts and another image for beam-hardening artifacts. This result is attainable because one type of image artifact (e.g., aliasing) will be inconsistent relative to another type of image artifact (e.g., beam-hardening). As such, the different artifact types will generally belong to different consistency classes that will be separated by the method of the present disclosure. Separating the artifacts into different artifact images is advantageous when information about the specific artifact sources can provide additional information As illustrated in FIG. 5, the above-described SMART RECON method can also be used to separate static and moving portions of an image or time series of images. Not only can the static and moving portions be separated, but the moving portions can be divided into two or more images depicting regions of the image field-of-view ("FOV") that are moving at different speeds. In this manner, regions of the image FOV that affected by different motion sources can be separated out. For instance, motion associated with respiration can be separated from cardiac motion or the motion of a tumor. As a result, respiratory or cardiac gating can be achieved without the need for additional processing or motion information acquisition.

Figure 6:
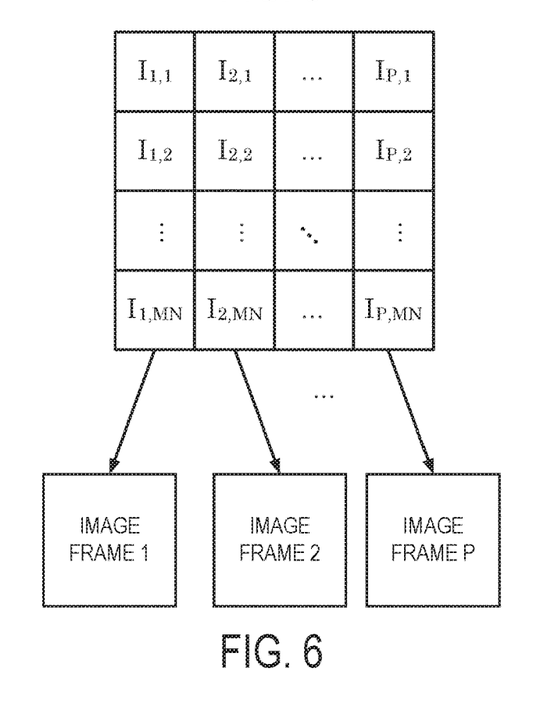
FIG. 6 is an illustration of an example of a rank-minimized image matrix having columns associated with different time frames obtained during a dynamic imaging acquisition, each of the different time frames corresponding to a different set of self-consistent data.

As illustrated in FIG. 6, the above-described SMART RECON method is also capable of reconstructing a series of image frames, such as a series of images depicting a vasculature during a time-resolved angiographic or perfusion imaging procedure, a subject's heart during a cardiac imaging procedure, a subject's respiration, and so on. In these instances, the method of the present disclosure is able to recover a set of consistent images of the subject acquired during the course of data acquisition. As one example, in cardiac imaging applications, the method can be used to produce motion consistent images for each cardiac phase because the data acquired at a given phase of the cardiac cycle will be largely consistent with other data acquired at the same cardiac phase, whereas data acquired at different cardiac phases will be largely inconsistent. The method can also be implemented in contrast-enhanced imaging applications to generate several consistent time frames from one short scan data acquisition, which can then be used to provide selectably-high temporal resolution, time-resolved, CT angiographic images. Such images are particularly useful for analyzing the cardiovascular structures, such as when guiding interventional procedures related thereto.

Figure 7:
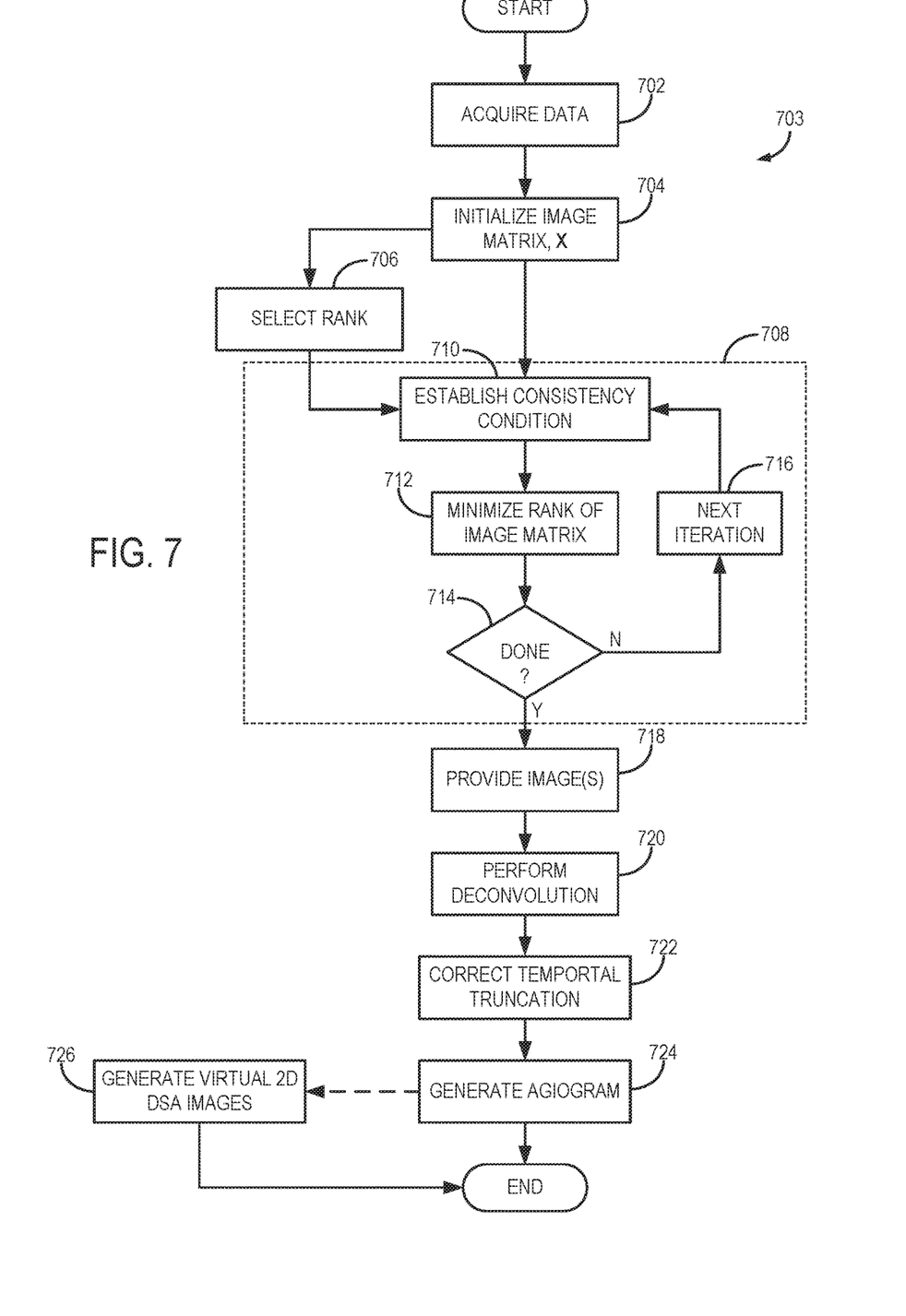
FIG. 7 is a flowchart of an example of a method for producing an image of a subject from data acquired using a CT imaging system in accordance with the present disclosure.

In particular, referring to FIG. 7, a flowchart setting forth the steps of an example of a method for producing an image in accordance with the present disclosure is illustrated. The method begins with the acquisition of data using a medical imaging system, as indicated at step 702. The data acquisition can be performed with any suitable medical imaging system, including an x-ray computed tomography system, an x-ray tomosynthesis system, or an x-ray C-arm system, or even a magnetic resonance imaging system, an ultrasound system, a positron emission tomography system, or the like.

In the present example, the acquisition may be performed by using a C-arm system, such as described above with respect to FIG. 1, or other system that is suitable for acquiring angiographic images, such as may be particularly useful for guiding interventional procedures. As will be described, the systems and methods of the present disclosure are capable of combining the images associated with a CT/angio-suite using systems that are not typically employed in CT/angio-suites, to provide information about soft tissue, angiography, and perfusion. More particularly, the data acquired at step 702 may be acquired using a so-called "short scan." As described herein, a "short scan" may refer to, for example, a CT acquisition that extends over approximately 180 degrees, plus the fan angle, which provides an approximate range of 200 degrees. However, greater ranges can be used, if desired. Likewise, in some situations it may be desirable to perform a short scan over an even shorter angular range, including so-called quarter-scans.

Acquiring data at step 702 may include acquiring data with and without the use of a vascular contrast agent. That is, step 702 may both a first C-arm acquisition with contrast and a time-resolved, cone beam angiographic acquisition to acquire selectively-high spatial and temporal resolution. Also, acquisitions can be designed to acquire only arterial data or only venous data. As one non-limiting example, acquiring data at step 702 may be achieved using approximately 10 sweeps of a C-arm system, such as illustrated in FIG. 1. However, this number of sweeps can be greatly reduced, such as to only 2 sweeps of the C-arm system—one with contrast enhancement via a vascular contrast agent, such as iodine, and one without contrast enhancement.

Figure 8:
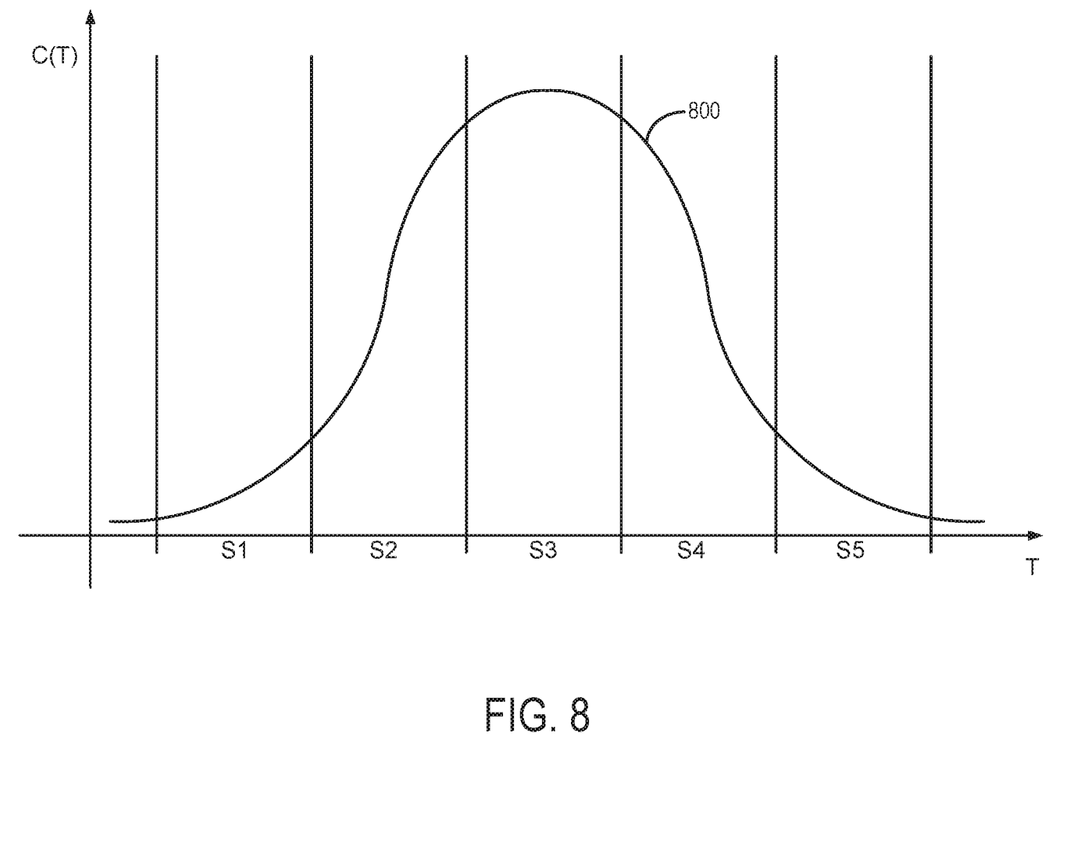
FIG. 8 is a graph illustrating one example for using a sliding temporal window to create segments for using in a reconstruction process in accordance with the present disclosure.

As a separate example, the scan may be performed over a time period of, as a non-limiting example, approximately 5 seconds to approximately 20 seconds. Referring to FIG. 8, a given sweep may be performed over a time "T" that can be divided into segments, in this example, 5 segments, S1-S5. In this way, a contrast curve 800 is divided into 5 sets of view angles, which, as will be described, may be treated equally during reconstructing (i.e., no weighting).

After data have been acquired, the image reconstruction process generally begins 703. First, an image matrix having column that will be associated with different images is initialized, as indicated at step 704, and as described above. Optionally, a desired rank to which the image matrix should be minimized is selected, as indicated at step 706. As discussed above, the choice of image matrix rank can be determined using a singular value decomposition of the image matrix. As indicated generally at 708, a target image of the subject is then reconstructed using SMART RECON or an iterative rank minimization process that is subject to a consistency condition constraint in which each column of the image matrix is required to be consistent with a unique subset of the acquired data that is to some extent inconsistent with the rest of the acquired data. That is, each column of the reconstructed image matrix will correspond to an image representative of a unique subset of the acquired data.

As described above, the data acquired at step 702 may be acquired using a "short scan." As such, the subsets may be selected based on the angular range of acquisition. Based on angular range, each of these subsets of the acquired data contain data that are consistent with each other, but at the same time, each subset of the acquired data contain data that are generally inconsistent with data not included in the subset. As such, the image reconstruction process is capable of automatically separating the acquired data into different subsets of data that each correspond to a unique consistency class. For example, in the example of FIG. 8, the data acquired at segment S1 is different in both view angle and contrast from the data acquired at segment S2. By minimizing the rank of the image matrix, the fewest possible number of such consistency classes is sought. As noted above, however, the desired image matrix rank can also be selected to force the separation of the acquired data into a predefined number of consistency classes.

The reconstruction of the image matrix, thus, includes establishing the aforementioned consistency condition between the columns of the image matrix and subsets of the acquired data, as indicated at step 710. The rank of the image matrix is then minimized, as indicated at step 712. Thus, a SMART RECON reconstruction is performed using finite temporal window defined by the angular range used to acquire the data.

This process is iteratively repeated until a stopping criterion is met, as determined at decision block 714. Examples of stopping criterion include when a target rank, which may be optionally selected as described above, is achieved, and when the difference of the estimated values in two consecutive iterations is smaller than a predetermined threshold value. If the stopping criterion is not met, the next iteration of the minimization begins, as indicated at step 716.

When the process of creating the initial images of the subject using SMART RECON 708 is complete, a set of images is provided at step 718 with a first, finite temporal window defined by the angular range of acquisition. At step 720, a temporal deconvolution is then applied to the reconstructed time-resolved cone beam CT images with the first, finite temporal window width to generate time-resolved cone beam CT images with a second temporal resolution that is higher than the first temporal resolution to provide the a selectivity in temporal resolution. Put another way, the time-resolved cone-beam CT images generated at step 720 define a continuous temporal sampling to provide the clinician with an infinitely high temporal resolution. That is, the images generated using SMART RECON provide definitive temporal behavior. As described above, the data for each segment is unweighted. Thus, the deconvolution performed at step 720 determines the true temporal behavior.

At step 722 the images generated in step 720 may be corrected for potential temporal truncation effects, such as caused by the limited data acquisition performed at step 702, such as by using the above-described short scan or other limited range of view angles. For example, this correction for potential temporal truncation may be performed using a gamma-variate fit that is applied to the images generated in step 720.

At step 724 a time-resolved angiogram is generated that defines a continuous temporal sampling. In particular, a time-resolved cone beam CT angiogram with the second, higher temporal resolution is generated by performing a mask subtraction, for example, using one of the first or last images acquired.

In some applications, step 724 may complete the process. Optionally, the angiograms generated at process step 724 may be used to create virtual 2D digital subtraction angiography (DSA) images. For example, a cone beam forward projection can be applied to the image series generated at step 724 to generate virtual 2D DSA images from any perspective angle.

As such, systems and methods are provided to simplify the way time-resolved images for interventional procedures are acquired and ease clinical workflow. The above-described systems and methods reduce radiation dose, contrast dose, and, as a result, enhance patient safety since only IV contrast injection is needed. The procedure can thus be performed at outpatient clinics.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for reconstructing an image using a cone-beam computed tomography (CT) imaging system, the steps of the method comprising:
    a) acquiring data from a subject with the CT imaging system using a limited scan range that is less than 360 degrees;
    b) initializing an image matrix having columns that each correspond to a different image;
    c) reconstructing at least one image of the subject having a first temporal resolution from the data acquired in step a) by:
        i) minimizing a matrix rank of the image matrix;
        ii) constraining the rank minimization of step c)i) subject to a consistency condition that promotes a forward projection of each column in the image matrix to be consistent with a different subset of the acquired data, each subset of the acquired data containing data that are consistent with each other while being inconsistent with data in other subsets of the acquired data;
    d) performing a temporal deconvolution of the at least one image using a finite temporal window to generate at least one image of the subject with a second temporal resolution that is greater than the first temporal resolution; and
    e) subtracting the at least one image of the subject with the second temporal resolution and a mask image of the subject to generate a time-resolved CT angiogram of the subject.

2. The method as recited in claim 1 in which the limited scan range is 200 degrees or less, including a fan angle.

3. The method as recited in claim 1 in which the CT imaging system generates a cone beam and wherein the at least one image of the subject with second temporal resolution includes time-resolved cone beam CT images with a continuous temporal sampling.

4. The method as recited in claim 1 further comprising performing a gamma-variate fit to the at least one image of the subject with the second temporal resolution to correct for potential temporal truncation effects caused by the limited scan range.

5. The method as recited in claim 1 further comprising f) applying a cone-beam forward projection to the time-resolved CT angiogram to generate a virtual 2D angiography image.

6. The method as recited in claim 1 in which step a) includes an acquisition with intravenous (IV) contrast and without contrast.

7. The method as recited in claim 1 in which the CT imaging system is a C-arm CT imaging system.

8. The method as recited in claim 1 in which the data acquired in step a) includes inconsistencies and step c) includes reconstructing a target image of the subject that is substantially free of image artifacts and at least one artifact image that contains substantially only image artifacts associated with the inconsistencies.

9. The method as recited in claim 1 in which the data acquired in step a) is representative of a time series of images and step c) includes reconstructing the time series of images, wherein each column in the image matrix corresponds to one of the images in the time series.

10. A method for reconstructing an image using a cone-beam computed tomography (CT) imaging system, the steps of the method comprising:

a) acquiring data from a subject with the CT imaging system, the acquired data acquired using a short scan of less than 360 degrees and containing a plurality of data consistency classes;

b) reconstructing an image of the subject from the data acquired in step a), the image of the subject containing artifacts associated with the data inconsistencies;

c) forming an image matrix having a first column corresponding to the image reconstructed in step b);

d) computing a target image matrix by iteratively updating the image matrix formed in step c) by minimizing a matrix rank of the image matrix subject to a data consistency condition such that each column of the computed target image matrix corresponds to a different one of the plurality of data consistency classes; and e) providing each column of the target image matrix computed in step d) as an image of the subject that is substantially free of artifacts to produce a series of images of the subject at a first temporal resolution;

f) deconvolving the series of images of the subject at the first temporal resolution using a finite temporal window to generate a series of images of the subject with second temporal resolution that is higher than the first temporal resolution; and g) subtracting the series of images of the subject with the second temporal resolution and from mask images of the subject to generate a time-resolved CT angiogram of the subject.

11. The method as recited in claim 10 in which the short scan has a range of 200 degrees or less, including a fan angle.

12. The method as recited in claim 10 in which the CT imaging system generates a cone beam and wherein the series of images of the subject with the second temporal resolution are time-resolved cone beam CT images that define a continuous temporal sampling.

13. The method as recited in claim 10 further comprising performing a gamma-variate fit to the series of images of the subject with the second temporal resolution to correct for potential temporal truncation effects caused by the limited scan range.

14. The method as recited in claim 10 further comprising h) applying a cone-beam forward projection to the time-resolved CT angiogram to generate a virtual 2D angiography image.

15. The method as recited in claim 10 in which step a) includes an acquisition with intravenous (IV) contrast and without contrast.

16. The method as recited in claim 10 in which the CT imaging system is a C-arm CT imaging system.

17. The method as recited in claim 10 in which the plurality of data consistency classes in the data acquired in step a) include a data consistency class for data consistent with a true image of the subject and a data consistency class for data consistent with at least one artifact.

18. The method as recited in claim 10 in which the plurality of data consistency classes in the data acquired in step a) include data consistency classes corresponding to data consistent with different physical states of the subject.

19. The method as recited in claim 10 in which the plurality of data consistency classes in the data acquired in step a) include data consistency classes corresponding to data consistent with different view angles of the data was acquired in step a).

20. A cone-beam computed tomography (CT) system comprising:

an x-ray source and associated detectors configured to acquire imaging data from a subject over a range of view angles;

a computer system including a processor configured to:

a) control operation of the x-ray source and associated detectors to acquire data from a subject with the CT imaging system using a limited scan range that is less than 360 degrees;

b) initialize an image matrix having columns that each correspond to a different image;

c) reconstruct at least one image of the subject having a first temporal resolution from the data acquired in step a) by:

i) minimizing a matrix rank of the image matrix;

ii) constraining the rank minimization of step c)i) subject to a consistency condition that promotes a forward projection of each column in the image matrix to be consistent with a different subset of the acquired data, each subset of the acquired data containing data that are consistent with each other while being inconsistent with data in other subsets of the acquired data;

d) perform a temporal deconvolution of the at least one image using a finite temporal window to generate at least one image of the subject with a second temporal resolution that is greater than the first temporal resolution; and e) subtract the at least one image of the subject with the second temporal resolution and a mask image of the subject to generate a time-resolved CT angiogram of the subject.

* * * * *